United States Patent
Vago (10) Patent No.: US 6,226,997 B1
(45) Date of Patent: May 8, 2001

(54) METHOD AND DEVICE FOR MAINTAINING TEMPERATURE INTEGRITY OF CRYOGENICALLY PRESERVED BIOLOGICAL SAMPLES

(75) Inventor: Robert E. Vago, Palm Harbor, FL (US)

(73) Assignee: Cryo-Cell International, Inc., Clearwater, FL (US)

( * ) Notice: Subject to any disclaimer, the term of this patent is extended or adjusted under 35 U.S.C. 154(b) by 0 days.

(21) Appl. No.: 09/456,279

(22) Filed: Dec. 7, 1999

(51) Int. Cl.[7] ....................................... F25B 49/00
(52) U.S. Cl. ..................... 62/130; 62/457.9; 340/586
(58) Field of Search .................... 62/125, 126, 127, 62/129, 130, 371, 372, 457.1, 157.2, 457.9; 236/94; 165/11.1; 340/584, 585, 586, 588; 374/141, 186

(56) References Cited

U.S. PATENT DOCUMENTS

| | | | |
|---|---|---|---|
| 3,589,139 | 6/1971 | Arthur | 62/115 |
| 4,262,494 | 4/1981 | Karow, Jr. | 62/384 |
| 4,459,825 | 7/1984 | Brouch | 62/404 |
| 4,739,622 | 4/1988 | Smith | 62/78 |
| 4,745,759 | 5/1988 | Bauer et al. | 62/127 X |
| 4,870,829 | 10/1989 | Oulette et al. | 62/51.1 |
| 5,325,678 | 7/1994 | Borah et al. | 62/129 X |
| 5,437,163 | 8/1995 | Jurewicz et al. | 62/130 X |
| 5,483,799 | 1/1996 | Dalto | 62/3.7 |
| 5,586,438 | 12/1996 | Fahy | 62/78 |
| 5,598,713 | 2/1997 | Bartilucci | 62/78 |
| 6,133,842 | 10/2000 | Gariepy | 340/689 |

FOREIGN PATENT DOCUMENTS

2225847   6/1990  (GB).

*Primary Examiner*—Harry B. Tanner
(74) *Attorney, Agent, or Firm*—R. Neil Sudol; Henry D. Coleman (57) ABSTRACT

A method for preserving the temperature integrity of cryogenically preserved biological samples is presented, involving initiating a countdown sequence upon removal of a sample from a controlled portable or bulk storage environment, requiring operator action to terminate the countdown on restoration of the sample to a controlled environment. Audible and visual warnings are provided to an operator prior to attainment of a critical temperature, beyond which damage may accrue to the sample. A portable device facilitating execution of the method is described.

22 Claims, 4 Drawing Sheets

METHOD AND DEVICE FOR MAINTAINING TEMPERATURE INTEGRITY OF CRYOGENICALLY PRESERVED BIOLOGICAL SAMPLES

FIELD OF THE INVENTION

This invention relates to a method and to an associated device or apparatus for maintaining the temperature integrity of cryogenically preserved materials. More particularly, this invention relates to a method and to an associated apparatus for safeguarding the cryogenic preservation of biological specimens during transfer of the specimens to or from a long-term storage container.

BACKGROUND OF THE INVENTION

When properly treated, biological specimens including human tissue and cell lines may be viably stored almost indefinitely at temperatures approaching that of liquid nitrogen, so long as that temperature is maintained. As long as a specimen is stored in a bulk storage facility it is relatively easy to maintain that specimen at a steady liquid nitrogen temperature. However, once the temperature of a specimen is raised significantly, the integrity of the specimen suffers. More specifically, unintended (upward) temperature excursions (UTE's), even falling far short of thawing, may permit the growth of ice crystals inside stored biological samples. Ice crystals may disrupt cell membranes, destroy cellular organelles and genetic material, and render the biological samples inviable. Such damage is irreversible and, if not recorded or reported at the time, may go undetected until the samples are deliberately thawed for use, years or possibly decades later.

When it becomes necessary to move or transfer a specimen, the possibility for uncontrolled and unrecorded temperature excursions occurs. The problem is compounded because an operator may not be aware that a removed specimen has undergone an unacceptable temperature excursion, or, inadvertently allowing such an excursion to occur, may not wish to record such an event out of concern for his or her continued employment and the possibly accurate perception that the damage is unlikely to be discovered during his or her tenure, or possibly, lifetime.

For these reasons, any installation undertaking the long-term cryogenic storage of viable tissue samples and cell lines must embody quality control and quality assurance measures, both to render unintended upward temperature excursions of stored material improbable, and to assure end-users of the improbability of such excursions and of the over-all reliability of the storage facility, to which irreplaceable samples may be entrusted. There is a continuing need for improved devices which will assist in maintaining the temperature integrity of biological samples undergoing cryogenic processing, and in particular, during operations which require the temporary removal of individual specimens from a controlled bulk storage facility and exposure to ambient conditions during such transfer, transportation, or other intermediate steps prior to a final deliberate thawing and use. There is yet a further need for methods and devices which will assure the temperature integrity of a multitude of portable individual samples within a bulk storage facility without the necessity of expensive sensing devices or permanent sensor leads affixed to each cell.

OBJECTS OF THE INVENTION

An object of the present invention is to provide a method and/or an apparatus for assisting in maintaining the temperature integrity of specimens stored at or within a preselected temperature range.

A more particular object of the present invention is to provide such a method and/or apparatus which will facilitate the maintenance of temperature integrity of cryogenically preserved biological specimens temporarily removed from a low-temperature storage container for processing or transport.

Yet another object of the present invention is to provide such a method and/or apparatus which will minimize possibilities for operator error during a processing operation requiring temporary removal of a cryogenically preserved biological specimen from a storage apparatus.

These and other objects of the present invention will be apparent from the drawings and descriptions herein.

SUMMARY OF THE INVENTION

The present invention addresses methods and devices for overcoming these limitations of bulk cryogenic storage facilities and in providing temperature control assurance, particularly for the storage of a multitude of small sub-containers (e.g., vials or ampules) which may be intermittently moved among units of the storage facility or between the facility and portable transport containers.

A bulk cryogenic storage facility includes one or more bulk containers or storage units each containing a multitude of addressable storage locations or receptacles for the receipt of vials or ampules. Such a bulk storage facility is disclosed in U.S. Pat. No. 5,921,102. A transfer operation comprises removing one or more vials containing cryogenically preserved biological material from respective storage locations and subsequently inserting the vials in different storage locations in the same or different bulk container or in a portable cryogenic storage unit. A portable cryogenic storage unit is a portable device capable of maintaining the temperature of one or more vials or other sub-containers in a cryogenic temperature range during transport. Typically, a portable cryogenic storage unit will take the form of an insulated container including a reservoir for liquid nitrogen, identifiable storage locations for one or more sub-containers, and a temperature monitoring device.

A method in accordance with the present invention for maintaining temperature integrity of a cryogenic specimen during a transfer operation comprises triggering an automatic process tracking the temperature of an individual specimen container upon removal of that container from a storage location in a bulk or portable cryogenic storage unit. In general, the temperature of the individual specimen container will rise following removal from a bulk or portable cryogenic storage unit. Upon exceeding a critical temperature $T_c$, irreversible damage is presumed to begin accumulating in the specimen. Therefore, prior to reaching temperature $T_c$, action is initiated at an alarm temperature $T_A = T_c - \Delta$, where $\Delta$ is a temperature increment pre-chosen to allow time for corrective action to be completed prior to incipient accumulation of irreversible specimen damage at temperature $T_c$.

Action initiated automatically upon determining that the temperature of a vial in transit has exceeded temperature $T_A$ may include sounding an audible alarm to alert a human operator to return the specimen to the bulk or portable cryogenic storage facility. Action initiated may also include issuance of instructions to a robotic arm to return the specimen to a storage location in a bulk or portable cryogenic storage facility, in conjunction with an audible alarm to alert a human operator to the impending automatic operation. In addition to operator or machine action, the temperature excursion may be recorded as an isolated event or as a portion of a complete temperature profile by a microprocessor associated with the bulk cryogenic storage facility (the "mainframe", although it may in general be a workstation or PC), or temporarily recorded by a microprocessor associated with the portable cryogenic storage facility, for subsequent transfer to the mainframe associated with the bulk cryogenic storage facility.

A temperature tracking operation in accordance with the present invention is implemented by a microprocessor or computer and may include extrapolation of a current temperature of a vial or other container exposed to ambient conditions from an initial temperature of the vial as maintained in the storage location. This extrapolation may be based upon an empirical study of a standard vial containing a material with thermal properties similar to those of a representative biological specimen. In that case, the extrapolation consists of a timing operation coupled with a look-up operation on a standard temperature curve.

Use may be made in implementation of the present invention of Newton's Law of Constant Cooling. The Law of Constant Cooling states roughly that heat transfer rate across an insulator is proportional to a temperature difference across that insulator and approximately independent of the absolute temperatures involved. As a consequence of this law, a wide variety of thermal relaxation problems involving the heating or cooling of a sample in an ambient bath will have solutions of the form:

$$T - T_{amb} = (T_0 - T_{amb}) e^{-\alpha(t-t_0)} \quad (1)$$

where $T_0$ is the sample temperature at time $t_0$, $T_{amb}$ is the ambient temperature, and $\alpha$ is a rate constant dependent on the detailed configuration but not on the temperature or time. The rate constant $\alpha$ may be determined empirically for a given sample content and container by a technician without undue experimentation, in a routine measurement operation. Ambient temperature may be monitored by a sensor affixed externally to a static or portable cryogenic storage device, or input by a technician from another source, whereas initial temperature $T_0$ may either be actively monitored or known from sample storage conditions, e.g. storage under liquid nitrogen. Finally, time $t_0$, time of initial exposure to ambient conditions, may be input by an operator or, in a preferred embodiment, automatically detected upon removal of a vial from a storage location in a cryogenic storage facility.

Thus a temperature tracking process may be automated, depending on a technician to input a vial type and contents type, amounting to a selection of $\alpha$, initial and ambient temperatures and time of initial exposure being automatically detected.

Triggering of a tracking operation during a cryogenic transfer operation in accordance with the present invention may comprise actuation of a mechanical switch partially in the form of a finger or detent sensing removal of an individual vial or ampule from a storage location, or the commencement of tracking may be signaled by positive feedback from a robotic arm commanded to remove a vial or ampule from a particular storage location, indicating that the ampule has in fact been removed.

Alternatively, a continuous monitoring of vial temperature may be effected via a real time temperature measurement of an individual unit or container. Preferably, the measurement is of an internal temperature of a vial or container in a region containing the biological specimen, rather than a surface measurement. Two methods of accomplishing this object are disclosed in connection with the present invention.

In the first instance, an electrical temperature sensing element, such as a silicon diode, a ruthenium oxide resistor, a gallium arsenide semiconductor or a thermocouple such as for example a Chromel (TM) Gold thermocouple, may be embedded in an individual storage container, or reference vial. A pair of leads is electrically attached to a pair of relatively rigid protruding studs protruding from the reference vial. Upon engagement by a robotic arm during a transfer operation, positive electrical contact is made with the embedded sensor, and a continuous temperature reading is obtained, corresponding to an internal temperature of the reference vial.

In a second instance, a sensor embedded in an individual reference container or vial does not require direct electrical connections for reading. Such a sensor element depends on bulk constitutive properties of a material, such as magnetic or electrical susceptibility, which forms part of an electric circuit together with coils disposed in a robotic arm or gripper, partially mediated by time-varying electromagnetic fields. Temperature at an interior location of the vial or container is then determined by electrical properties of the total circuit, similarly to cases in the first instance, where the variable electrical properties are resistance or electromotive force, but not requiring a direct mechanical connection to complete the circuit.

In a basic embodiment of a method and device in accordance with the present invention, a sample or specimen is initially enclosed within a portable transport container or crystal in an identifiable storage location. A microprocessor attached to the transport container is programmed with the identifier (e.g., bar code) of each specimen associated with a storage location in the transport container. Upon manual withdrawal of a specimen container from the transport container by a technician, a mechanical detent/switch assembly, or other sensing device, delivers a signal to the microprocessor. Using a stored empirically determined temperature curve or equation as discussed previously, an extrapolated temperature of the specimen is determined as a function of elapsed time from withdrawal. The extrapolated temperature may optionally be displayed by a readout attached to the transport container. Upon the extrapolation reaching a preset alarm temperature, $T_A$, an audible alarm is sounded, alerting the technician to the necessity of either returning the specimen to the transport container or depositing the specimen in an alternate cryogenically controlled environment.

In the event of insertion of the specimen in a receptacle in a location different from the transport container, the technician presses a button on the transport container, silencing the alarm. Simultaneously, insertion of the specimen in a second location is recorded by an associated microprocessor. Eventually, data from the transport unit associated microprocessor, regarded as a peripheral unit, may be transferred to a microprocessor associated with a second location when that location is a bulk storage location, which microprocessor may be regarded as a mainframe unit; thereby accumulating a complete thermal specimen history on the mainframe.

A cryogenic transport device in accordance with the present invention minimally includes at least one identifiable storage location for a vial or ampule, a microprocessor, a means of inputting the identity of a vial inserted into a storage location to the microprocessor, a means of detecting and inputting to the microprocessor a withdrawal of a vial from a storage location located in the cryogenic transport device, and programming enabling the microprocessor to track an internal temperature of the withdrawn vial.

In a second embodiment of a method in accordance with the present invention, a specimen is initially stored in an identified location in a bulk cryogenic storage facility. Upon withdrawal of the sample from its storage location by a robotic arm, the withdrawal event is recorded by an associated central microprocessor or mainframe computer. The event may either be identified by actuation of a mechanical switch on withdrawal of the sample, or from proprioceptive feedback from the robotic arm, which, arriving at a known location and grasping with a predetermined force an object of known size is presumed to have grasped a specimen vial. Both techniques may be combined for quality assurance.

The withdrawal initiates a tracking process, which associates with the withdrawn specimen at each subsequent time increment a presumed temperature. The temperature is again determined by extrapolation using a pre-recorded empirically determined temperature curve or equation. Alternatively, the instantaneous temperature at an internal point of the vial is determined by the output of one or more sensors attached to or embedded in the vial, and engaged by circuitry in the robotic arm, as discussed above.

As before, tracking is continued until the specimen is returned to the original or an alternative storage location in the original or another bulk cryogenic storage unit, or the central microprocessor or mainframe receives input indicating the specimen has been transferred out of the bulk storage system, as for example to a transport unit, or to controlled thawing. As tracking continues a measured or extrapolated alarm temperature $T_A$ may be reached. This event sounds an audible alarm for a storage facility operator, is recorded on a thermal history of the instant specimen by the mainframe, and, if the specimen is still under control of the robotic arm, initiates automatic actions to return the specimen to its original or another available storage location.

DESCRIPTION OF THE PREFERRED EMBODIMENTS

Figure 1:
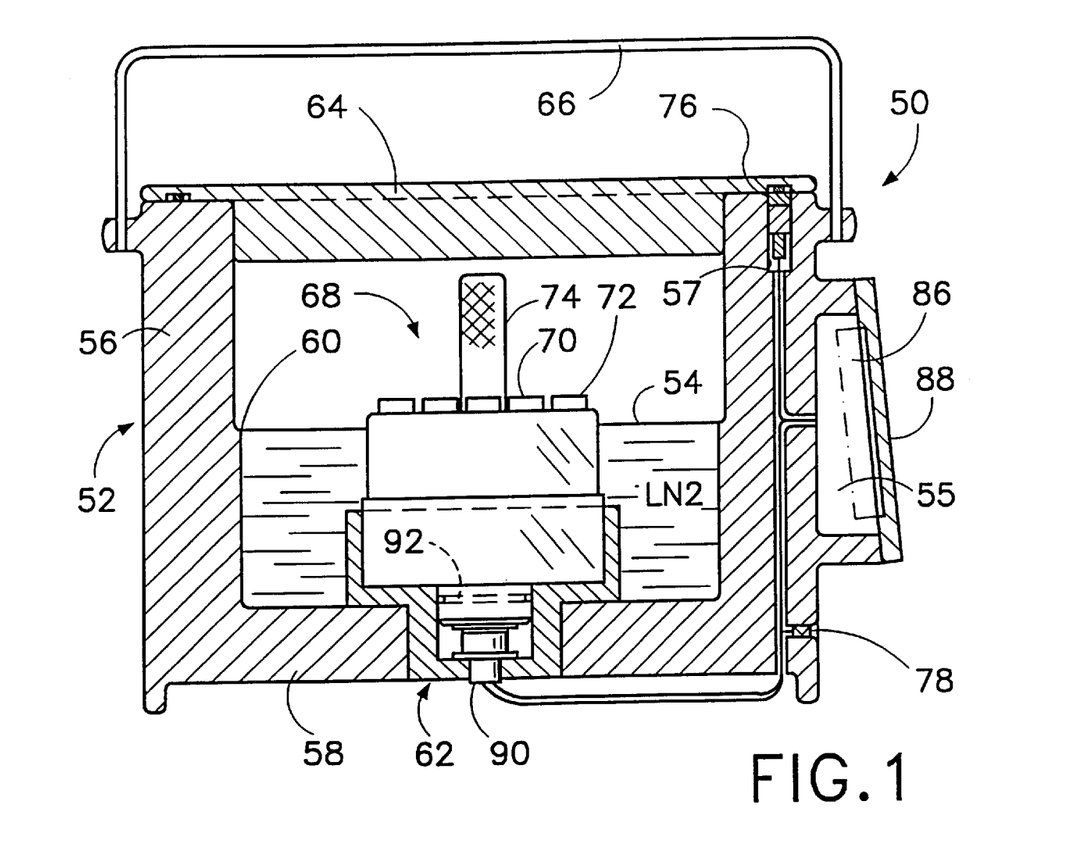
FIG. 1 is a cross-sectional view of a cryogenic transport device in accordance with the present invention.

A cryogenic transport container generally shown at 50 in FIG. 1 comprises a lid 64 and a flask 52. Flask 52 contains a reservoir of LN2 (liquid nitrogen) 54 or other cryo-coolant, initially filled to a fill line marked by an inside lip or shoulder 60 of a sidewall 56 of flask 52. A microprocessor 86 mounted in a recess 55 in an outer surface (not designated) of sidewall 56 executes a temperature estimation process when a vial 70, 72 is removed from transport container 50. To that end, microprocessor 86 is wired to a proximity sensor 76 disposed in a pocket 57 in a upper surface of the sidewall. Proximity sensor 76 alerts microprocessor 86 as to the opening of lid 64, a convenient arbitrary commencement time for a vial removal and transfer operation. To carry out its temperature estimation function, microprocessor 86 also relies on or utilizes initial temperature values provided by an external or room temperature thermocouple 78 and via an electrical penetrator or feed through 90 also wired to the microprocessor.

A bracket assembly 62 is disposed in a floor 58 of flask 52 for receipt of a Vial Temporary Storage Holder (VTSH) generally shown at 68. VTSH 68 is provided with a handle 74 and storage locations or receptacles (not shown in this view) for vials 70, 72 etcetera and is removably mounted in bracket assembly 62 inside transport container 50. An O-ring 92 substantially excludes LN2 from a recess (not separately designated) enclosing penetrator 90.

Figure 2:
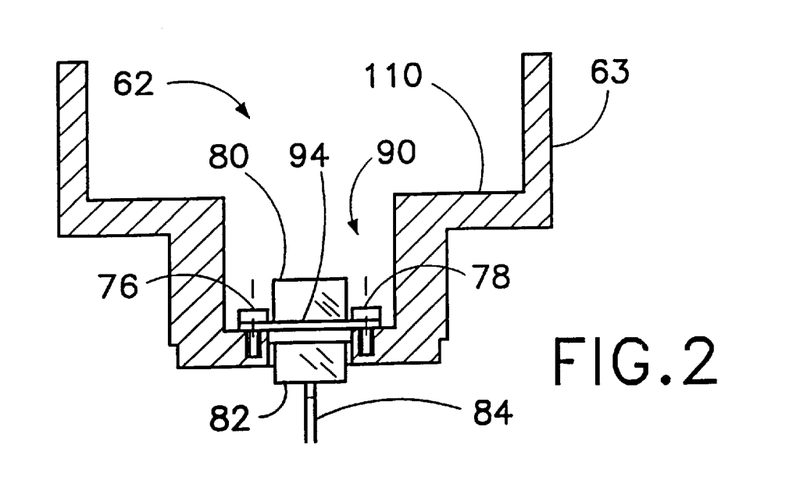
FIG. 2 is a cross-sectional view of a bracket included in the transport device of FIG. 1.

Bracket assembly 62 is shown in greater detail in FIG. 2. A bracket body 63 constitutes a principal structural member of bracket assembly 62. Inside body 63 is an upwardly facing surface 110 which engages a lower face 105 (FIG. 3) of a central body 104 of VTSH 68 to substantially support the VTSH.

Electrical penetrator 90 comprises an upper connector 80 and a lower connector 82 joined at a cover plate 94 in turn attached to bracket body 63 via bolts 76, 78. Cover plate 94 does not form a gas tight seal with bracket body 63, so that any cryo-coolant leaking past O-ring 92 may vent when vaporized and not lift the Vial Temporary Storage Holder from bracket assembly 62. The primary purpose of the O-ring is to contain the liquid nitrogen, and not to keep the liquid nitrogen away from electrical penetrator 90, which is unnecessary, as liquid nitrogen forms an excellent insulator. The electrical penetrator however necessarily forms a hot spot in flask 52, so that it is advantageous to limit the amount of LN2 present in this area in order to minimize losses by boiling. A standard order of assembly of (discussed below) of a cryogenic transport container 50 (FIG. 1) mounts a VTSH 68 to an instrumented thermally-insulated flask 52 prior to filling the flask with liquid nitrogen, thereby first forming a seal at O-ring 92 and substantially excluding LN2 from the vicinity of penetrator 90, as previously indicated.

Leads 84 carry a voltage signal to microprocessor 86 from an internal thermocouple (described below) contained in the VTSH 68. This voltage signal from the internal thermocouple enables microprocessor 86 to monitor pre-transfer or initial temperatures of vials held in the VTSH 68, while the voltage signal from external sensor or thermocouple 78 enables microprocessor 86 to monitor ambient temperatures. These temperatures are displayed under the control of microprocessor 86 on a combination keypad and display at 88. In addition to providing microprocessor 86 with an alert signal on removal of lid 64 from flask 52, the proximity sensor provides the microprocessor with an indication that a vial has been removed from the VTSH 68 when the vial is passed over the sensor by a technician in a procedure to be described hereinafter.

Figure 3:
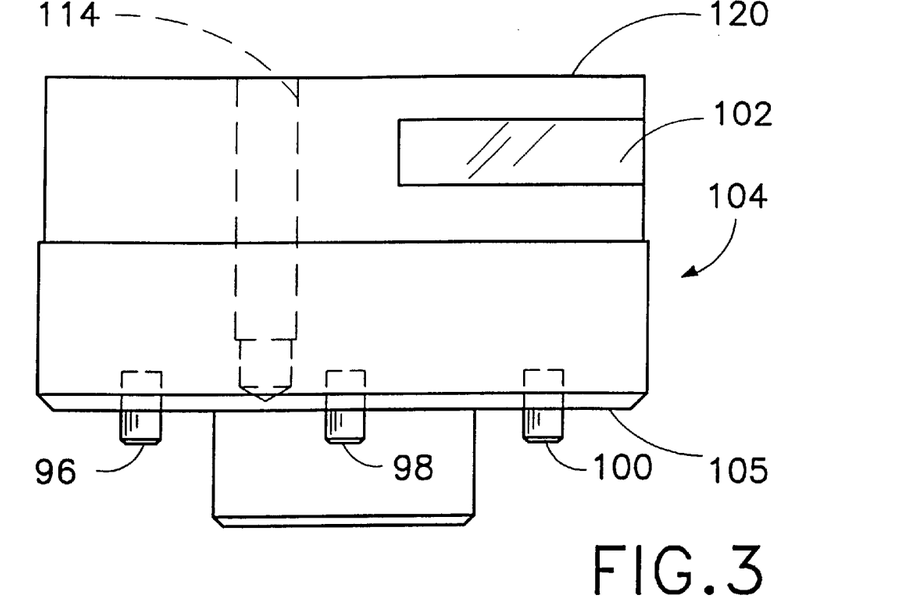
FIG. 3 is an elevational view of another component of the device of FIG. 1.
Figure 4:
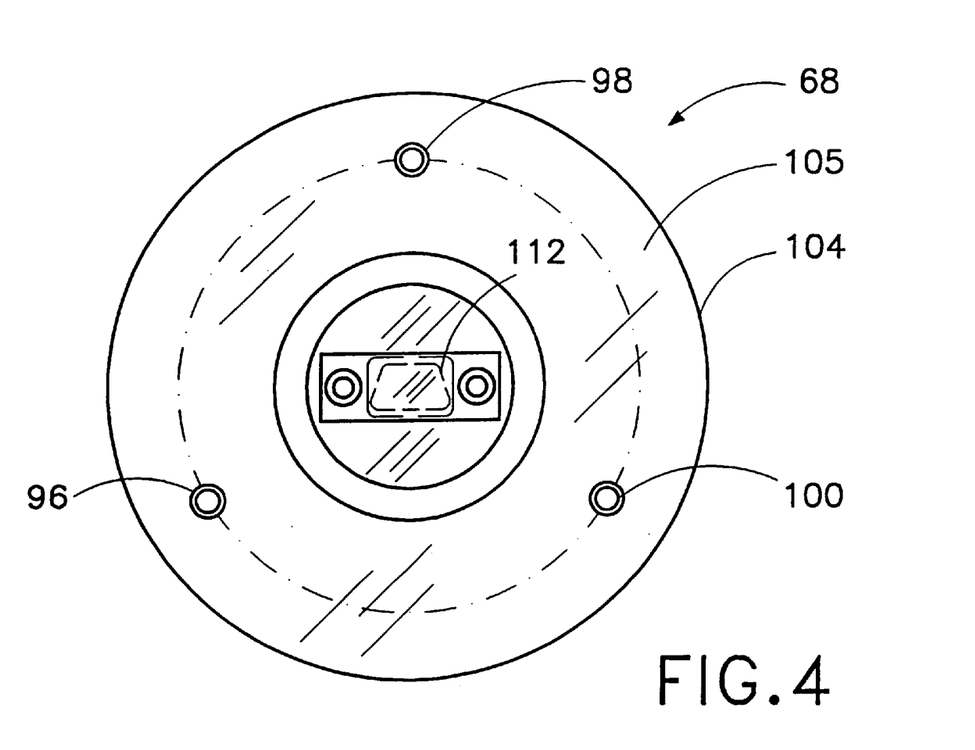
FIG. 4 is a bottom plan view of the component of FIG. 3.
Figure 5:
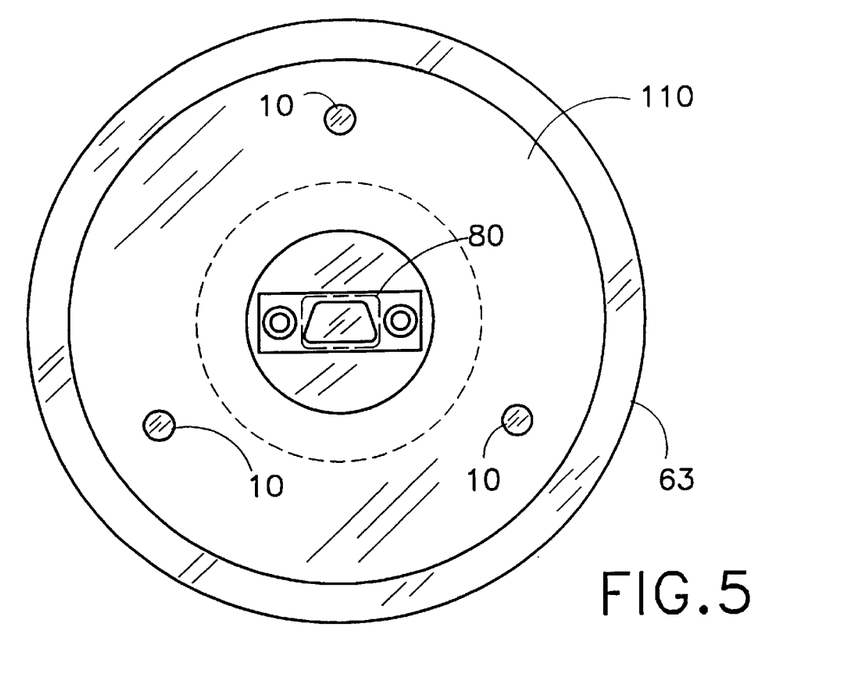
FIG. 5 is a top plan view of the bracket of FIG. 2.
Figures 7, 8, 9, 10:
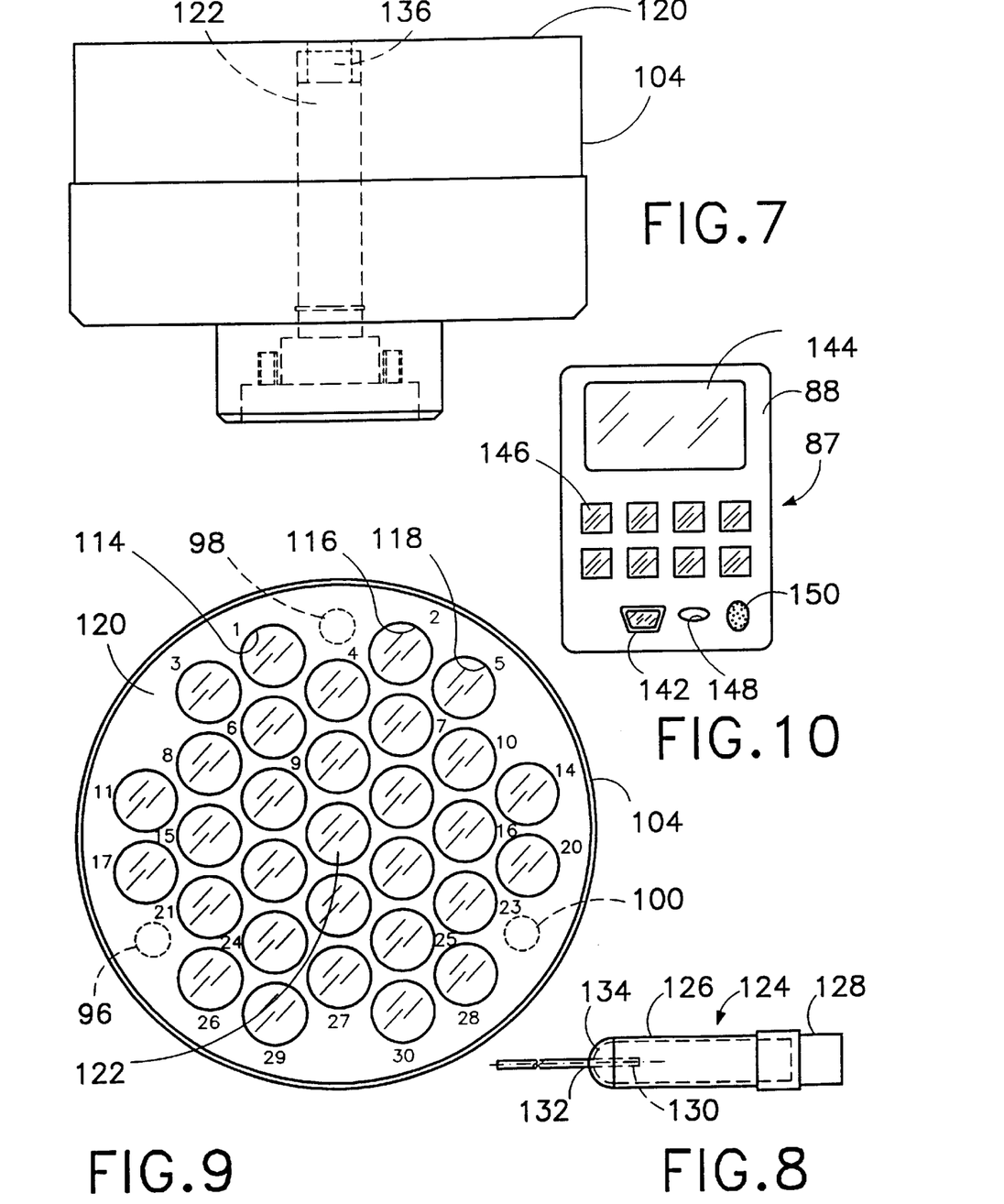
FIG. 7 is a further elevational view of the component of FIG. 3, showing additional interior detail.
FIG. 8 is a schematic of the instrumented sample container of FIG. 6.
FIG. 9 is a top elevational view of the component of FIGS. 3 and 7.
FIG. 10 is a schematic elevation of a display and keypad of the device of FIG. 1.

FIGS. 3 and 7 respectively show details of a generic temporary vial storage receptacle 114 and a special central storage receptacle 122 in central body 104. The body 104 of Vial Temporary Storage Holder 68 is conveniently formed by machining from a single block of material, with the exception of studs 96, 98, 100 and a face plate 102 (FIG. 3). Studs 96, 98, 100 are mounted on lower face 105 of VTSH body 104 and engage in sockets 106, 107, 109 in upwardly facing surface 110 of bracket body 63 (FIG. 5), to ensure positive alignment of an electrical connector 112 mounted on VTSH 68 and lower connector 80 of electrical penetrator 90. Face plate 102 is provided with a bar code or other machine readable symbols (not illustrated) for enabling automatic identification of a particular VTSH 68 among a plurality of such units. Multiple VTSH are in general interchangeable and may form a repetitive sub-unit in a larger cryogenic mass storage system (not illustrated).

VTSH 68 is provided with a plurality of temporary storage receptacles 114, 116, 118 et alia (FIGS. 3, 9) recessed below an upper surface 120 of body 104. As shown in FIG. 9, storage receptacles 114, 116, 118, etc., are provided with respective numerical designations "1", "2", "3", . . . , "30" engraved on surface 120 and filled with a low-temperature durable black compound. This enumeration is appropriate for prototyped dimensions and standard available brand of 2.0 ml cryogenic vials. However, an alternative VTSH may be constructed for use with standard 5.0 ml vials. Special central storage receptacle or bore 122 is not so enumerated, and is reserved for holding a reference container 124 (FIG. 8).

Reference container 124 is optionally formed from a NUNC 5000-0020, 2.0 ml liquid capacity, sterile polypropylene cryogenic vial 126 with a high density polyethylene cap 128. Vial 126 is filled with a cell sample emulating mixture (not shown) consisting of a cellular medium such as RPMI 1640 and a smaller fraction of a cryoprotectant such as Dimethyl Sulfoxide (DMSO). The sample emulating mixture closely matches the composition and thermal properties of vials containing actual cellular samples and is additionally equipped with a copper-constantan or other cryo-temperature adapted thermocouple 130 inserted through a hole 132 drilled in a base or bottom end 134 of vial 126, subsequently sealed and pressure tested at hole 132. The arrangement of reference container 124 in special storage receptacle 122 of VTSH body 104 is illustrated in FIG. 6.

Container or vial assembly 124 is inserted in reserved storage receptacle 122 in body 104. Reserved receptacle 124, unlike sample storage receptacles 114, 116, 118, et al. (not illustrated in FIG. 6), is drilled through a bottom surface (not designated) of body 104, as well as through top surface 120. Assembly 124 is inserted and sealed in receptacle or bore 122 with a cryo-adapted adhesive. An aperture 136 is fitted from an underside with a plug or insert 140, secured from top side or surface 120 with a cap 138, together securely holding reference container 124 in conjunction with electrical connector 112.

Figure 6:
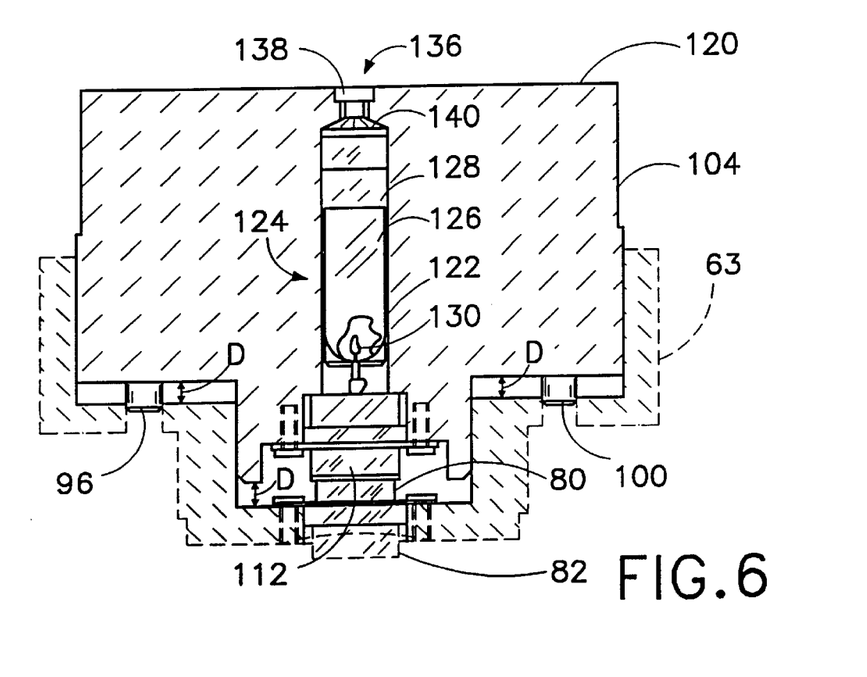
FIG. 6 is a cross-sectional view of the component of FIG. 3 mounted in the bracket of FIG. 2, showing an instrumented sample container.

FIG. 6 also illustrates body 104 of VTSH 68 in a partially inserted position in bracket body 63 of bracket assembly 62, a distance D from a fully engaged configuration. Studs 96, 100 are shown partially inserted in sockets 106, 109 and VTSH mounted connector 112 is shown engaged with upper connector 80 of bracket mounted electrical penetrator 90. A positive engagement and resulting defined positions of storage receptacles 114, 116 etc. relative to cryogenic transport container 50 facilitates eventual automatic execution or robotization of a transfer process.

FIG. 10 shows a detail of key pad and display or interface panel 88 for operator/external interface with microprocessor 86. The interface panel includes a dot matrix-type liquid crystal display (LCD) 144 and keys or touchpads 146 etc. forming a touch sensitive keyboard or keypad 87. The term "keypad" is used herein to refer to an array of touch-sensitive keys, while the keys individually are referred to as "touchpads." Panel 88 also contains an RS-232 jack 142 for connection to an external data-processing device, for example, for transferring thermal history information to an external computer (not illustrated). A battery (not illustrated) provides power for electronics associated with the cryogenic transport device, including microprocessor 86 and display 144; the status of the battery is indicated by possible energization or illumination of low-battery status indication 148. Coincident with illumination of low-battery status indication 148, detailed instructions for battery replacement are made available to a technician or operator on display 144 following pressure activation of a "Batt." touchpad (not illustrated). Alternatively, low-battery status could be indicated on LCD matrix display 144, removing a need for battery status indication 148. A miniature speaker or tone-generator 150 provides audible status and warning signals under control of microprocessor 86, operating under a stored machine program.

The appearance of the keypad (FIG. 10) is schematic and not to be taken as limiting to the appearance of a particular data-entry pad on a specific embodiment of the invention.

A detailed procedure for preserving temperature integrity of cryogenically preserved samples during a transfer operation is described. For the purposes of this disclosure, the term "temperature integrity" refers in a first sense to the maintenance of samples in an acceptable temperature band during a processing operation and in a second sense to the maintenance of an electronic audit trail plausibly assuring an end-user that temperature integrity in the first sense has in fact been maintained. Positive temperature integrity, or the state wherein temperature integrity has not been compromised, thus involves elements of both quality control and of quality assurance; that is, positive temperature integrity means both that physical temperature limits have not been passed and that a sufficiently credible certification of this fact exists for a given set of economic circumstances.

An operator is charged with the responsibility of safe-handling a cryogenically processed cellular sample and is provided with means to ensure maintenance of temperature integrity of the sample while moving it through a non-cryogenic, e.g., room-temperature, environment from one cryogenic storage location to another. The temperature estimation process described herein utilizes the physical relationship which exists between elapsed time and accumulated temperature rise of a cellular sample vial, such as a 2 milliliter or 5 milliliter vial, when the vial is removed from a cryogenic temperature and placed into a room temperature environment for an indeterminate time period. It is contemplated to provide both a warning that an extrapolated sample temperature is about to pass a critical temperature threshold and a permanent record of a temperature excursion during a transport event.

In a preparation stage of a Standard Operating Procedure (SOP) for executing a controlled cryogenic transfer utilizing cryogenic transport container 50, an operator or cryotechnician will assemble or gather the following components: the VTSH 68, the instrumented thermally-insulated flask 52 and lid 64, and a pair of metal ratcheting forceps (not illustrated) for grasping, holding and releasing a vial. VTSH 68 is introduced into the flask 52, as illustrated in FIGS. 1 and 6. The VTSH may accommodate either 2 ml or 5 ml sample vials in a standard embodiment. For fully automated operation a height detection device (not shown) would be incorporated in the VTSH to detect vial size, whereas in a partially manual implementation of a cryogenic transfer operation, a technician can determine vial size by visual inspection or record consultation and press an appropriate button. A simplified operation would avoid mixing vial sizes in a single VTSH, although it is not inconsistent with the objects of the invention to do so.

A vial size selection is subsequently input via keypad 87, allowing microprocessor 86 to select a correct time vs. temperature relationship. Subsequently, with lid 64 removed, the flask 52 is filled with liquid nitrogen to the inside lip or fill line 60 (FIG. 1). Lid 64 is attached to flask 52 to close container 50 following filling thereof. According to the SOP, the technician shall keep transport container 50 within reach during a cryogenic transfer procedure.

During a first stage of a cryo-preservation procedure, a source of a cellular material may either be at or above room temperature, as from a fresh tissue preparation, or be packed in ice, thereby exhibiting an initial temperature in an approximate range of 0° to 37° C. A cellular sample prepared from the source of cellular material is subsequently encapsulated in a cryoadapted vial nominally of either 2 ml or 5 ml capacity, the vial subsequently being provided with a unique Sample Identification Number (SIN) which may be affixed to the vial in the form of a bar code. The vial is additionally filled with a mixture consisting substantially of a cellular nutrient medium such as RPMI 1640 and a smaller fraction of a cryoprotectant compound such as Dimethyl Sulfoxide (DMSO), as is known in the cryogenic arts. The encapsulated sample is placed in a programmable controlled cooling rate freezer (not illustrated) for a defined regimen of cooling from an initial sample temperature to an intermediate processing temperature of −95 degrees C.

In a second stage of a cryo-preservation procedure, sample capsules or vials pre-cooled in the controlled cooling rate freezer are transferred to a cryogenic transport device for transport to a long-term cryogenic storage facility. Prior to commencement of a transport operation, the cryogenic transport device is moved to the location of the controlled cooling rate freezer. Following attainment of the intermediate processing temperature in the controlled cooling rate freezer, lid 64 is removed from flask 52, exposing VTSH 68 which is pre-positioned and pre-cooled within the cryogenic transport device. The vial is placed in the Vial Temporary Storage Holder (VTSH) 68, in one of a set of vial hole receptacles or temporary storage receptacles 114, etc. The temporary storage receptacles are identified with temporary storage receptacle numerals, as described above with reference to FIG. 9. The relationship of a sample identification number (SIN) to a vial temporary storage receptacle numeral is recorded by entry on the touch pad and display 88. Removal of lid 64 from flask 52 transmits a ready signal to microprocessor 86 via actuation of proximity switch or sensor 76. Following receipt of the ready signal, microprocessor 86 drives LCD 144 to display ancillary instructions necessary to effect vial transition. Multiple vials may be inserted in the VTSH 68 following removal of the flask lid 64.

Following insertion of a last vial into VTSH 68 in flask 52, an action subsequently signaled by reinstallation of lid 64, touchpads or keys 146, etc., associated with vial transition are deactivated for a 15 minute wait period to allow inserted vials to cool to temperature of the liquid nitrogen or other cryo-coolant 54. During this 15 wait minute period, microprocessor 86 causes a visible countdown to be displayed on LCD 144 and also sounds an audible signal signifying the end of the countdown period and accordingly readiness for vial transfer. Transport container 50 may be moved from a vicinity of the controlled cooling rate freezer to a vicinity of the long-term cryogenic storage facility during the wait period, in preparation for a transfer of sample vials from the transport device to the long-term storage facility.

During a third and final stage of a cryo-preservation procedure, transport container 50 is positioned within arm's length of a cryogenic operator in turn positioned within arm's length of an access port of the long term storage facility (not illustrated). The pair of metal ratcheting forceps is also positioned within reach of the operator. Following expiry of the 15 minute wait period, the microprocessor driven LCD 144 will alternately display the temperature of the vials 70, 72 contained within VTSH 68 and the temperature of the ambient air. These temperatures must be within prescribed limits prior to initiation of a second vial transfer. Microprocessor 86 will advise the cryogenic operator, via LCD 144, when either the vial temperature or the ambient temperature is outside of the prescribed limits and optionally suggest corrective action.

Prior to removal of a vial 70, 72 or lid 64 from the transport container 50, the operator depresses a TS (transition start) touchpad (not designated) on keypad 87. Detailed step by step instructions for commencement of a vial transfer operation are displayed on LCD 144 as an aid to the cryogenic operator. The identity of a given vial as either a 2 ml or a 5 ml vial remains stored in microprocessor 86 from the required preparation stage of a controlled cryogenic transfer utilizing cryogenic transport container 50. Following activation of the TS touchpad, the operator then removes and sets aside the flask lid 64, triggering a first signal from proximity sensor 76, and subsequently manipulates the aforementioned forceps to grasp a vial of choice from VTSH 68. The metal forceps are passed over the proximity sensor in the course of a removal of the vial 70, 72 from the transport container 50, which triggers generation of a second signal inducing microprocessor 86 to start either the 2 ml or the 5 ml countdown period. Successful activation of the proximity sensor is signaled to the operator by an audible signal or "beep" emitted by speaker or tone generator 150. In the event of a failure of audible confirmation of a sensor activation, the operator must by procedure try again until a signal is heard, or, after a predetermined number of trials, return the vial to the VTSH.

During the selected countdown period, microprocessor 86 executes an automatic process tracking the temperature of the removed vial 70, 72. In general, the temperature of a removed vial 70, 72 will rise following removal from portable cryogenic container 50. Prior to the attainment by the removed vial 70, 72 of a critical temperature $T_c$, as estimated by microprocessor 86, the microprocessor undertakes preventative action at an alarm temperature $T_A=T_c-\Delta$, where $\Delta$ is a temperature increment pre-chosen to allow time for corrective action to be completed prior to incipient accumulation of irreversible specimen damage at temperature $T_c$.

Microprocessor extrapolates a current temperature of the removed vial 70, 72 from an initial temperature of the vial as maintained in storage and transport container 50. This extrapolation may be based upon empirical data or upon a mathematical formula. Empirical data is obtained using a standard vial which contains a material with thermal properties similar to those of a representative biological specimen. In that case, the extrapolation or estimation process executed by microprocessor 86 includes a timing operation coupled with a look-up on a standard temperature curve, table or other data storage device. A sample mathematical formula utilizable by microprocessor 86 is Newton's Law of Constant Cooling. This law states roughly that heat transfer rate across an insulator is proportional to a temperature difference across that insulator and approximately independent of the absolute temperatures involved. The law takes the form:

$$T - T_{amb} = (T_0 - T_{amb}) e^{-\alpha(t - t_0)} \quad (2)$$

where $T_0$ is the sample temperature at time $t_0$, $T_{amb}$ is the ambient temperature, and $\alpha$ is a rate constant dependent on the detailed configuration but not on the temperature or time. The rate constant $\alpha$ may be determined empirically for a given sample content and container by a technician in a routine measurement operation. As discussed above, ambient temperature $T_{amb}$ is monitored by external or room temperature thermocouple 78, whereas initial temperature $T_0$ is monitored via thermocouple 130 in reference container 124. Exposure onset time $t_0$ is automatically detected by microprocessor 86 in response to a signal transmitted from proximity sensor 76 upon removal of a vial 70, 72 from transport container 50.

A Touchpad Access Time-Delay feature inhibits LCD 144 and touchpad keys 146 for approximately 15 seconds after a vial 70, 72 is removed from the VTSH 68 for vial transfer. After initiation of and during this delay, microprocessor 86 generates a 3 digit random set of numerals, which are not displayed until the time delay is over. A flashing line of dashes is displayed by LCD 144 until the programmed 15-second delay period has elapsed. When the vial transfer operation is complete, the cryogenic operator presses and holds down a TC (transition complete) touchpad (not designated) on keypad 87 and keys in the 3 digit random set of numerals in sequence, which stops the countdown period and induces a display on LCD 144 of the warmest temperature attained by the vial during the transition or transport operation. The cryogenic operator records this temperature against the vial's predetermined identification, or SIN, and this information is also stored in electronic form in a memory of microprocessor 86 for possible subsequent download via a data cable (not shown) attached to RS-232 jack or port 142. Detailed step by step procedures for completion of a vial transfer operation are displayed on LCD 144 following pressure activation of the TC touchpad, similarly to display of instructions for commencement of a vial transfer operation following pressure activation of the TS touchpad.

In addition to visual indications appearing on LCD 144, audible indications are provided on speaker or tone-generator 150 as an aid to the cryogenic operator or technician. Once a transition operation countdown is commenced, following activation of the proximity sensor by lid removal and a sequential activation by proximal passage of sample bearing forceps, a steady tone is initiated and persists on speaker 150. A pulsed tone is generated when an extrapolation by microprocessor 86, based on vial size, internal and ambient temperatures, indicates 5 seconds remain to attainment of a critical vial temperature of −130° centigrade. At the critical temperature, the sound changes to a swept tone, indicative of an alarm condition, which persists until actuation of the TC keypad by the operator.

Behavior of visual display or LCD 144 mimics audible indications, beginning to flash 5 seconds before estimated attainment of a critical temperature by the sample. Since, by procedure, the transport device 50 with removed lid 64 and exposed VTSH 68 remains at arm's length of the technician during a vial transfer procedure, a 5 second warning provides adequate time for the technician to abort the transfer operation and return the 70, 72 vial to the safe environment of the VTSH in the event that an unforseen difficulty prevents completion of the transfer to the long term bulk cryogenic storage facility.

Further automation of a vial transfer procedure would include greater utilization of the RS-232 data port to communicate vial removal and receipt events between microprocessor 86 and an off-device computer; for example, a computer integrated with robotic operation of a bulk cryogenic long-term storage facility (not illustrated). Bar codes or other machine readable codes placed on individual vials 70, 72 as well as the VTSH 68 or VTSH's, provide further automation opportunities. It may also be envisaged that individual sample vials may carry respective sensors, for example, solid state devices having electromagnetic properties which change as a function of temperature. In that case, the sensors are queried by ancillary sensors or pick-ups located in a robotic arm functioning as a component of a bulk-cryogenic storage facility or located in an alternative instrumented version of a racheting forceps for use by a cryogenic operator. The instrumented forceps would communicate with either a cryogenic transfer device or a bulk cryogenic storage facility via a data cable or other data transfer means.

Although the present invention has been described in terms of specific embodiments and procedures to facilitate understanding and demonstrate feasible enablement, the person skilled in the art will readily conceive of equivalent embodiments and methods. For example, microprocessor 86 may utilize either a partially calculated cooling (warming) curve based on Newton's law of constant cooling, or a fully empirically evaluated cooling curve. Similarly, the invention may be understood to be equally applicable to a transfer of a vial from a portable device to a bulk storage facility, or from a bulk storage facility to a portable device, or other similar operations; the functionality inherent in microprocessor 86 or the cryogenic transport container 50 being fully or partially transferred to devices ancillary to the bulk storage facility or to other cryogenic storage containers, or a centralized location in a particular operating environment populated with both fixed and portable instrumented storage devices.

Accordingly, the embodiments and methods specifically disclosed herein are therefore not to be understood to be limiting to the scope of the invention as claimed.

What is claimed:

1. A quality control method for use in the transfer or conveyance of temperature sensitive material, comprising:
   providing a temperature-controlled storage container;
   providing at least one sub-container disposed in said storage container;
   removing said sub-container from said storage container; and
   upon the removing of said sub-container from said storage container, automatically tracking changes in temperature of said sub-container.

2. The method defined in claim 1 wherein the tracking of changes in temperature of said sub-container includes operating a computer or microprocessor to automatically estimate said changes in temperature pursuant to a predetermined rule or algorithm.

3. The method defined in claim 2 wherein the tracking of changes in temperature of said sub-container includes feeding to said computer or microprocessor encoded information including an ambient temperature and a temperature of said sub-container at the time of removal of said sub-container from said storage container, the operating of said computer or microprocessor including:

measuring a time interval commencing with removal of said sub-container from said storage container; and determining an estimated temperature of said sub-container in accordance with the measured time interval and a difference between said ambient temperature and the temperature of said sub-container at the time of commencement of said time interval.

4. The method defined in claim 3 wherein said encoded information further includes a size or volume of said sub-container, the determining of said estimated temperature including taking said size or volume into account.

5. The method defined in claim 4 wherein the feeding of said encoded information to said computer or microprocessor includes manually entering said size or volume via an input device connected to said computer or microprocessor.

6. The method defined in claim 3 wherein the feeding of said encoded information to said computer or microprocessor includes automatically transmitting a temperature-encoding signal from a temperature sensor to said computer or microprocessor.

7. The method defined in claim 3 wherein said encoded information further includes a volume of a specimen stored in said sub-container, the determining of said estimated temperature including taking said volume into account.

8. The method defined in claim 2 wherein said computer or microprocessor is mounted to said storage container.

9. The method defined in claim 2 wherein said rule or algorithm is empirically derived.

10. The method defined in claim 1, further comprising:

comparing a temperature of the removed sub-container with a predetermined threshold level; and returning said sub-container to said storage container upon determining that the temperature of said sub-container has attained said threshold level.

11. The method defined in claim 1 wherein said storage container is a first storage container, further comprising placing the removed sub-container in a second storage container, the tracking of changes in temperature of said sub-container being executed during a transfer of said sub-container from said first storage container to said second storage container.

12. The method defined in claim 1, further comprising generating a signal upon determining that the temperature of said sub-container has attained a threshold level.

13. The method defined in claim 1 wherein the removing of said sub-container from said storage container includes operating a robot assembly to automatically entrain said sub-container.

14. The method defined in claim 1 wherein said storage container is portable and thermally insulated, further comprising conveying said storage container to a predetermined location, the removing of said sub-container being performed while said storage container is disposed at said predetermined location.

15. The method defined in claim 1 wherein said storage container is provided with a display and a temperature sensor, further comprising operating said display to indicate a temperature detected by said sensor.

16. The method defined in claim 1, further comprising automatically recording a history of the tracked temperature of said sub-container.

17. An apparatus for use in the transfer or conveyance of temperature sensitive material, comprising:

a portable thermally insulated storage container;

a temperature sensor attached to said storage container for measuring a temperature of contents of said storage container; and a microprocessor attached to said storage container, said microprocessor being operatively connected to said sensor for receiving temperature readings therefrom, said microprocessor including temperature determination means for executing a temperature estimation process upon a removal of a sub-container from said container; and a trigger operatively coupled to said microprocessor for initiating said temperature estimation process upon a removal of a sub-container from said storage container.

18. The apparatus defined in claim 17, further comprising means operatively coupled to said microprocessor for feeding to said microprocessor an encoded ambient temperature, said temperature determination means including a timer measuring a time interval commencing with removal of said sub-container from said storage container, said temperature determination means further including programmed circuits for estimating a temperature of said sub-container in accordance with the measured time interval and a difference between said ambient temperature and a temperature from said temperature sensor.

19. The apparatus defined in claim 18 wherein said temperature determination means further includes programmed circuits for estimating the temperature of said sub-container in part based on a size or volume of said sub-container.

20. The apparatus defined in claim 17 wherein said microprocessor includes means for comparing a temperature of a removed sub-container with a predetermined threshold level and for generating a signal to effectuate a return of said sub-container to said storage container upon a determination that the temperature of said sub-container has attained said threshold level.

21. The apparatus defined in claim 17 wherein said microprocessor includes means for automatically recording a history of the estimated temperature of said sub-container.

22. The apparatus defined in claim 17, further comprising a display attached to said storage container, said display being operatively connected to said sensor for indicating a temperature detected by said sensor.

* * * * *